United States Patent
Okamura et al.

(10) Patent No.: US 11,125,742 B2
(45) Date of Patent: Sep. 21, 2021

(54) NON-SPECIFIC REACTION INHIBITOR, METHOD FOR INHIBITING NON-SPECIFIC REACTION, AND KIT

(75) Inventors: Yoshikazu Okamura, Tokyo (JP); Shigeru Tashiro, Tokyo (JP)

(73) Assignee: LSI MEDIENCE CORPORATION, Tokyo (JP)

( * ) Notice: Subject to any disclaimer, the term of this patent is extended or adjusted under 35 U.S.C. 154(b) by 118 days.

(21) Appl. No.: 14/129,510

(22) PCT Filed: Jun. 28, 2012

(86) PCT No.: PCT/JP2012/066484
§ 371 (c)(1),
(2), (4) Date: Dec. 26, 2013

(87) PCT Pub. No.: WO2013/002309
PCT Pub. Date: Jan. 3, 2013

(65) Prior Publication Data
US 2014/0193842 A1    Jul. 10, 2014

(30) Foreign Application Priority Data

Jun. 29, 2011  (JP) .............................. JP2011-144464

(51) Int. Cl.
*G01N 33/53* (2006.01)
*C07D 207/416* (2006.01)

(52) U.S. Cl.
CPC ..... *G01N 33/5306* (2013.01); *C07D 207/416* (2013.01)

(58) Field of Classification Search
CPC ................................................ C07D 207/416
See application file for complete search history.

(56) References Cited

U.S. PATENT DOCUMENTS

| | | | |
|---|---|---|---|
| 5,169,754 A * | 12/1992 | Siiman ...................... | B03C 1/01 427/131 |
| 5,525,524 A | 6/1996 | Buechler et al. | |
| 5,658,725 A | 8/1997 | Schlieper et al. | |
| 5,863,740 A | 1/1999 | Kientsch-Engel et al. | |
| 5,952,185 A | 9/1999 | Huber et al. | |
| 6,777,190 B1 * | 8/2004 | Buechler ............ | C07D 207/416 424/178.1 |
| 7,338,809 B2 | 3/2008 | Yokoi | |
| 2006/0035837 A1 | 2/2006 | Altieri et al. | |
| 2008/0171693 A1 | 7/2008 | Altieri et al. | |

FOREIGN PATENT DOCUMENTS

| | | |
|---|---|---|
| CN | 101065138 A | 10/2007 |
| EP | 2 184 608 A1 | 5/2010 |
| EP | 2184608 A1 * | 5/2010 .......... G01N 33/531 |
| JP | 2006-177914 | 7/2006 |
| JP | 2006-308307 | 11/2006 |
| JP | 4571999 B1 | 10/2010 |
| WO | 92/18868 A1 | 10/1992 |
| WO | 03/065042 A1 | 8/2003 |
| WO | 2005/098051 A2 | 10/2005 |

OTHER PUBLICATIONS

Ishikawa et al., "Preparation of Monomeric Fab'-Horseradish Peroxidase Conjugate Using Thiol Groups in the Hinge and Its Evaluation in Enzyme Immunoassay and Immunohistochemical Staining," Annals of the New York Academy of Sciences, vol. 420, pp. 74-89, published Dec. 16, 2006.*
Ortega-Munoz et al., "Vinyle sulfone functionalized silica: a ready to use" pre-activated material for immobilization of biomolecules J. Mater. Chem., vol. 20, pp. 7189-7196, published 2010.*
Merriam-Webster, print retrieved Mar. 31, 2017.*
Thermo Scientific, <https://assets.thermofisher.com/TFS-Assets/LSG/manuals/MAN0011295_SMCC_SulfoSMCC_UG.pdf>, print retrieved Dec. 8, 2017.*
Phaneuf, et al.; Covalent linkage of recombinant hirudin to poly-(ethylene terephthalate) (Dacron): creation of a novel antithrombin surface; Biomaterials 1997; vol. 18, No. 10.
International Search Report of PCT/JP2012/066484, dated Sep. 11, 2012.
Extended European Search Report, dated Jun. 15, 2015, EP Application No. 12803782.7.

* cited by examiner

*Primary Examiner* — Tracy Vivlemore
*Assistant Examiner* — Nam P Nguyen
(74) *Attorney, Agent, or Firm* — Kilpatrick Townsend & Stockton LLP

(57) ABSTRACT

Provided is a non-specific reaction inhibitor for achieving the accurate detection and quantitation of a trace component (a target substance) contained in a sample, in an immunoassay, by simply and effectively inhibiting a non-specific reaction associated with the measurement.
The non-specific reaction inhibitor comprises a substance of the formula I:

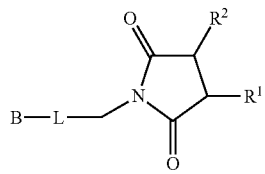

wherein $R^1$ and $R^2$ together form a double bond between carbons, to which they are respectively bonded directly, or $R^1$ is a hydrogen atom and $R^2$ is a group formed by removing H from an SH-group-containing compound, B is a support, and L is a spacer arm portion.

5 Claims, No Drawings

NON-SPECIFIC REACTION INHIBITOR, METHOD FOR INHIBITING NON-SPECIFIC REACTION, AND KIT

CROSS-REFERENCE TO RELATED APPLICATIONS

This application is a national phase application under 35 U.S.C. 371 claiming priority to PCT/JP2012/066484, filed Jun. 28, 2012, which application claims priority to JP 2011-144464, filed Jun. 29, 2011, the teachings of which are hereby incorporated by reference in their entireties for all purposes.

TECHNICAL FIELD

The present invention relates to a non-specific reaction inhibitor, which is used in an immunoassay, for inhibiting a non-specific reaction that hinders the accurate detection and quantization of a trace amount of a target substance; a method for inhibiting a non-specific reaction using the non-specific reaction inhibitor; and an immunoassay kit comprising the non-specific reaction inhibitor.

BACKGROUND ART

An immunoassay based on an antigen-antibody reaction is widely used in clinical examinations, because a trace component to be measured can be specifically detected or accurately measured. In such an immunoassay, it is often observed that the reliability of measured values is impaired, due to non-specific reactions other than a specific antigen-antibody reaction with a target substance, as the original purpose. This phenomenon is caused by reacting a component(s) contained in the assay system with a component(s) other than the target substance (antigen) contained in a sample.

Until now, various attempts have been made in order to inhibit the non-specific reactions and obtain accurate measured values. For example, a pretreatment of samples to be assayed by heating or with an appropriate reagent; an addition of a serum derived from various animals, an immunoglobulin fraction, albumin, skim milk, gelatin, surfactants, or the like to the assay system; or the like have been commonly carried out. In order to avoid a non-specific reaction caused by binding to the Fc portion of an antibody, as the rheumatoid factor, the use of an antibody fragment, such as Fab, F(ab')$_2$, or the like, in the specific reaction has been carried out. Further, an addition, to the assay system, of a monoclonal antibody which has a reaction specificity different from that of a monoclonal antibody used in the assay system and which does not inhibit reactions involved in the assay system, has been carried out.

Further, use of streptavidin cross-linked/polymerized using maleimide or the like, as shown in Patent literature 1, or a use of acylated protein aggregates, as shown in Patent literature 2, are known. Further, it is known that the first antibody labeled with a detectable substance, the second antibody, and a sample are reacted with one another in the presence of an N-substituted maleimide compound, and as a result, a non-specific binding of the detectable substance with a thiol group (i.e., an SH group) contained in the sample is inhibited (Patent literature 3). Further, it is disclosed that, in a method of inhibiting a non-specific adsorption of a biological-related molecule(s) to a carrier with a chemically modifying group selected from the group consisting of an N-hydroxysuccinimide ester group, a carboxyl group, a maleimide group, and an amino group on its surface, a blocking agent containing polyalkylene oxide with a functional group which can react with the chemically modifying group on the carrier and which is selected from the group consisting of an N-hydroxysuccinimide ester group, a mercapto group, and an amino group at its end(s) is used (Patent literature 4).

However, these methods have shown a certain degree of inhibitory effect to the non-specific reactions, but the effect was still insufficient for some samples, and thus, it was not satisfactory yet in the field of clinical examinations in which an erroneous diagnosis would lead to serious consequences.

CITATION LIST

Patent Literature

[Patent literature 1] Japanese Patent No. 3027770
[Patent literature 2] Japanese Translation Publication (Kohyo) No. 8-506907
[Patent literature 3] Japanese Patent No. 4571999
[Patent literature 4] Japanese Unexamined Patent Publication (Kokai) No. 2006-308307

SUMMARY OF INVENTION

Technical Problem

Under these circumstances, an object of the present invention is to provide a non-specific reaction inhibitor, a method of using the same, and an assay kit for achieving the accurate detection and quantization of a trace component (a target substance) contained in a sample, in an immunoassay, by simply and effectively inhibiting a non-specific reaction associated with the measurement.

Solution to Problem

The present inventors conducted intensive studies on a non-specific reaction in order to solve the problem, and as a result, found that the influence due to an interfering substance (a non-specific reaction substance) contained in a sample could in fact be avoided by adding a carrier protein, to which a substance with a maleimide group (Sulfo-SMCC: sulfosuccinimidyl-4-(N-maleimidomethyl)cyclohexane-1-carboxylate, or Sulfo-HMCS: N-(8-maleimidocapryloxy) sulfosuccinimide) was bound, to a reaction solution, and the present invention was completed. That is to say, as described in detail in the Examples, it was found that a substance which reacted with a carrier protein, to which a maleimide group was bound, existed in a sample, as the non-specific reaction substance. In the present invention, a non-specific reaction inhibitor, an assay method using the non-specific reaction inhibitor, and an assay reagent for the accurate measurement of a target substance in a sample were all completed, based on these findings.

The present invention relates to:
[1] a non-specific reaction inhibitor for an immunoassay, comprising a substance of the formula I:

[Chem. 1]

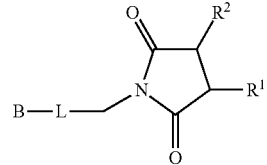

Wherein $R^1$ and $R^2$ together form a double bond between carbons to which they are respectively bonded directly, or $R^1$ is a hydrogen atom and $R^2$ is a group formed by removing H from an SH-group-containing compound, B is a support, and L is a spacer arm portion;

[2] the non-specific reaction inhibitor of [1], wherein the support is a carrier protein or a solid phase carrier;

[3] the non-specific reaction inhibitor of [2], wherein the carrier protein is albumin;

[4] the non-specific reaction inhibitor of [2], wherein the solid phase carrier is a group of particles;

[5] an immunoassay using the non-specific reaction inhibitor of any one of [1] to [4];

[6] the immunoassay of [5], wherein the immunoassay is a latex agglutination optical measurement method, an enzyme immunoassay, a nephelometric immunoassay, an enzyme-linked immunosorbent assay, a fluorescence immunoassay, or a radioimmunoassay;

[7] the immunoassay of [5] or [6], wherein a sample is reacted with the non-specific reaction inhibitor, before an immunological reaction specific for a target substance containing the sample is carried out;

[8] the immunoassay of [5] or [6], wherein an immunological reaction specific for a target substance containing a sample is carried out in the presence of the non-specific reaction inhibitor;

[9] the immunoassay of [5] or [6], wherein the immunoassay is a measurement by a sandwich method, and one or more steps of immunological reactions specific for a target substance containing a sample is carried out in the presence of the non-specific reaction inhibitor;

[10] an immunoassay kit comprising the non-specific reaction inhibitor of any one of [1] to [4].

Advantageous Effects of Invention

According to the non-specific reaction inhibitor, the method using the same, and the immunoassay kit of the present invention, the influence due to the non-specific reaction substance contained in samples can be simply and effectively inhibited, and thus, a trace component (a target substance) contained in these samples can be accurately measured.

The non-specific reaction substance found in the present invention reacts well with the non-specific reaction inhibitor of the present invention, in which a support (in particular, a protein) is coupled with a maleimide group or its derivative, and thus, the effect is especially high, when a support with which a maleimide group or its derivative is coupled exists during the specific immunological reaction. Therefore, it is considered that the present invention is especially effective in a reagent prepared by immobilizing or labeling an antibody or antigen using a maleimide method selected among immunoassays.

DESCRIPTION OF EMBODIMENTS

The non-specific reaction inhibitor of the present invention may be used in a known immunoassay.

Examples of the immunoassay include a single radial immunodiffusion method, a nephelometry, a nephelometric assay, an agglutination method, a radioimmunoassay, an enzyme immunoassay, and a fluorescence immunoassay. The radioimmunoassay, the enzyme immunoassay, and the fluorescence immunoassay show high measurement sensitivity, and are preferable for the measurement of trace components.

The radioimmunoassay, the enzyme immunoassay, and the fluorescence immunoassay are methods using labeled antibodies prepared by coupling a radioactive substance, an enzyme, and a fluorescent substance, respectively, with an antibody which specifically reacts with a target substance, and they are generally used in a solid phase method, in which an immobilized antibody or an immobilized antigen prepared by coupling an antibody or antigen with an insoluble carrier is combined with the labeled antibody. Examples of the solid phase method include a sandwich method in which an "immobilized antibody-antigen-labeled antibody" complex is formed and measured, and a competitive method based on the principle that a free antigen contained in a sample and the immobilized antigen competitively react with a certain amount of labeled antibodies added to a reaction system.

Examples of a sample used in the present invention include body fluids, such as whole blood, serum, plasma, cerebrospinal fluid, and saliva, urine, and feces extract.

A target substance is not limited, so long as it has an immunological reactivity, and there is a possibility that it is contained in a sample, but a substance useful in the diagnosis of diseases or understanding of conditions is preferable. Examples of the target substance include a hepatitis B virus surface antigen (HBsAg), a hepatitis C virus (HCV) antibody and antigen, a human immunodeficiency virus (HIV) antibody, a human T-cell leukemia virus-1 (HTLV-1) antibody, and a *Treponema pallidum* (TP) antibody, as well as various myocardial markers (creatine kinase (CKMB), myoglobin, and troponin), various hormones, and serum proteins.

The non-specific reaction inhibitor of the present invention comprises, as a non-specific reaction inhibitory substance, a substance of the formula I, in which a support is coupled directly or indirectly with a maleimide group or its derivative. The term "a derivative of a maleimide group" as used herein means a maleimide group (which reacts with a sulfhydryl group) blocked with an SH-group-containing compound. The support is not limited, so long as it is a substance inactive in an assay system (hereinafter sometimes referred to as a carrier), and examples of the support include a protein and a solid phase carrier. Examples of a carrier protein include albumin (bovine serum albumin: BSA and human serum albumin: HSA), inactivated alkaline phosphatase (inactivated ALP), inactivated horseradish peroxidase (inactive HRP), streptavidin, avidin, gelatin, casein, and antibodies. Examples of the solid phase carrier include a microtiter plate, a test tube, beads, particles, nanoparticles, and a membrane. Examples of the particles include magnetic particles, hydrophobic particles such as polystyrene latex, copolymer latex particles having a hydrophilic group such as an amino group, a carboxyl group, or the like on its surface, red blood cells, and gelatin particles. The term "inactive in an assay system" means that it does not affect an immunological reaction, an enzymatic reaction, or the like with a substance to be measured. An artisan skilled in the art can appropriately select a suitable carrier according to an assay principle.

The carrier protein may be purified from a biological sample or prepared as a preferred protein by genetic recombination.

The coupling of the maleimide group with the carrier protein may be carried out using a known cross-linking agent. So long as the cross-linking agent contains the maleimide group and a functional group for coupling with the carrier protein (for example, an amino-group-reactive functional group, a carboxyl-group-reactive functional group, and biotin), the cross-linking agent may have a cyclic or linear functional group between the maleimide group and the carrier protein.

Examples of the cross-linking agent which may be used include, as the cross-linking agent with an amino-group-reactive functional group, a compound of the formula: S-L-M (wherein S is an amino-group-reactive functional group, M is a maleimide group, and L is a spacer arm portion), more particularly, succinimidyl 4-[N-maleimidomethyl]cyclohexane-1-carboxylate (SMCC), sulfosuccinimidyl 4-[N-maleimidomethyl]cyclohexane-1-carboxylate (Sulfo-SMCC), succinimidyl-4-[N-maleimidomethyl]cyclohexane-1-carboxy-[6-amidocaproate](LC-SMCC), N-[e-maleimidocaproyloxy]succinimide ester (EMCS), N-[e-maleimidocaproyloxy]sulfosuccinimide ester (Sulfo-EMCS), N-[γ-maleimidobutyryloxy]succinimide ester (GMBS), N-[γ-maleimidobutyryloxy]sulfosuccinimide ester (Sulfo-GMBS), N-(11-maleimidoundecanoyloxy)succinimide (KMUS), N-[k-maleimidoundecanoyloxy]-sulfosuccinimide ester (Sulfo-KMUS), m-maleimidobenzoyl-N-hydoxysuccinimide ester (MBS), m-maleimidobenzoyl-N-hydoxysulfosuccinimide ester (Sulfo-MBS), succinimidyl 4-[p-maleimidophenyl]butyrate (SMPB), sulfosuccinimidyl 4-[p-maleimidophenyl]butyrate (Sulfo-SMPB), N-[α-maleimidoacetoxy]succinimide ester (AMAS), N-[β-maleimidopropyloxy]succinimide ester (BMPS), succinimidyl-6-[β-maleimidopropionamido]hexanoate (SMPH), N-(8-maleimidocapryloxy)succinimide (HMCS), and N-(8-maleimidocapryloxy)sulfosuccinimide (Sulfo-HMCS).

Examples of the cross-linking agent with a carboxyl-group-reactive functional group include a compound of the formula: H-L-M (wherein H is an carboxyl-group-reactive functional group, M is a maleimide group, and L is a spacer arm portion), more particularly, β-maleimidopropionic acid hydrazide (BMPH), 3,3'-N-[e-maleimidocaproic acid]hydrazide (EMCH), N-[k-maleimidoundecanoic acid]-hydrazide (KMUH), 4-[4-N-maleimidophenyl]butyric acid hydrazide hydrochloride (MPBH), and 3-[2-Pyridyldithio]propionyl hydrazide (PDPH).

Examples of the cross-linking agent with biotin include a compound of the formula: X-L-M (wherein X is biotin, M is a maleimide group, and L is a spacer arm portion), more particularly, 1-Biotinamido-4-[4"-(maleimidomethyl)cyclohexanecarboxamido]butane (Biotin-BMCC), maleimide-PEG11-Biotin, and maleimide-PEG2-Biotin.

The length of the spacer arm portion in the cross-linking is similar to that of a conventional cross-linking agent, for example, 4 to 52 Å, preferably 9 to 20 Å.

The coupling with these cross-linking agents may be carried out in accordance with a known method. After coupling with the cross-linking agent, the maleimide group may be blocked with an SH-group-containing compound (for example, a protein or an amino acid) by a known method. The SH-group-containing compound is not limited, so long as it is a compound which has an SH group and is capable of reacting with the maleimide group via the SH group to block the reactivity to the maleimide group.

The coupling of the maleimide group with the carrier particles may be carried out using a compound with a maleimide group during the preparation of the carrier particles; or may be carried out, using a compound with an amino group or a carboxyl group, by further coupling with a cross-linking agent having an amino-group-reactive functional group or a carboxyl-group-reactive functional group and a maleimide group; or may be carried out by coupling with a carrier protein having a maleimide group. The coupling of the carrier protein with the carrier particles prepared may be carried out by physical adsorption or covalent bonding. A known compound, or the above-mentioned cross-linking agent, may be used.

The assay principle of the present invention may use the above-mentioned immunoassay.

An antibody which may be used in the immunoassay may be a polyclonal antibody or a monoclonal antibody, and an antibody derived from any animal species which produces an antibody, for example, a rabbit, a goat, a sheep, a pig, a horse, a rat, or a mouse, may be used.

Examples of the antibody which may be used include a whole antibody and an antibody fragment prepared by digesting it with an enzymatic treatment or a chemical treatment, such as $F(ab')_2$ or Fab'.

In a sandwich method, in which an "immobilized antibody-antigen-labeled antibody" complex is formed and measured, these antibodies are immobilized on a solid phase carrier or to a labeled substance. Examples of the solid phase carrier include a microtiter plate, a test tube, beads, particles, nanoparticles, and a membrane. Examples of the particles include magnetic particles, hydrophobic particles such as polystyrene latex, copolymer latex particles having a hydrophilic group such as an amino group, a carboxyl group, or the like on its surface, red blood cells, and gelatin particles. Among these particles, magnetic particles are most preferable due to the achievement of a quick and convenient B/F separation. More particularly, magnetic particles of microparticles made of, for example, $Fe_3O_4$, $Fe_2O_3$, or various ferrites; metals such as iron, manganese, nickel, cobalt, chromium, and the like; or alloys such as cobalt, nickel, manganese, and the like may be preferably used. Further, a carrier in which these magnetic particles are immobilized on the surface of, or contained within polymer latex made of polystyrene or the like, gelatin, liposome, or the like may be preferably used. Examples of the membrane include a nitrocellulose membrane, a cellulose filter paper, and a nylon membrane, and a test piece of a simple assay kit based on immunochromatography or the like may be used.

Examples of the labeling substance, which may be used in the immunoassay, include an enzyme, a fluorescent substance, a radioactive isotope, and insoluble particles. Examples of the enzyme for labeling include alkaline phosphatase, peroxidase, glucose oxidase, tyrosinase, and acid phosphatase. Examples of the fluorescent substance include fluorescein isothiocyanate (FITC), green fluorescent protein (GFP), and luciferin. Examples of the isotope include $^{125}I$, $^{14}C$, and $^{32}P$.

When the labeling substance is an enzyme, the labeling substance may be measured by carrying out a luminescence, fluorescence, or coloring reaction using a substrate for the enzyme. For example, when the enzyme is alkaline phosphatase, a chemiluminescent substrate, such as CDP-star (registered trademark)(disodium 4-chloro-3-(methoxyspiro{1,2-dioxetane-3,2'-(5'-chloro)tricyclo[$3.3.1.1^{3,7}$]decane}-4-yl)phenyl phosphate), CSPD (registered trademark) (disodium 3-(4-methoxy-spiro{1,2-dioxetane-3,2-(5'-chloro)tricyclo[$3.3.1.1^{3,7}$]decane}-4-yl)phenyl phosphate), AMPPD (registered trademark) (3-(4-methoxyspiro{1,2-dioxetane-3,2'-tricyclo[$3.3.1.1^{3,7}$]decan}-4-yl)phenyl phosphate, APS-5, or the like; a fluorescent substrate, such as 4-methylumbelliferylphosphate or the like; or a coloring substrate, such as p-nitrophenyl phosphate, BCIP (5-bromo-4-chloro-3-indolyl phosphate), NBT (4-nitro-blue tetrazolium chloride), INT (iodo-nitrotetrazolium), or the like may be used as its substrate.

The above-mentioned antibody (or its fragment) may be used alone, or together with other polymers, such as proteins, polysaccharides, or synthetic polymers, to prepare a conjugate via an organic chemical method, an interaction based on biological affinity, or the like, in accordance with a method known from references.

In the organic chemical method, the conjugate may be prepared by forming a covalent bond using a cross-linking agent. Examples of the cross-linking agent include carbodiimides, isocyanates, diazo compounds, benzoquinone, glutaraldehyde, periodic acid, N-hydroxysuccinimide ester compounds, maleimide compounds, and pyridyl disulfide compounds. The preparation of the conjugate using these cross-linking agents may be carried out in a similar fashion to, for example, a method of coupling an antibody with an enzyme to prepare an enzyme-labeled antibody, which is described in detail in Ishikawa et al., "Kouso Meneki Sokutei-hou (Enzyme Immunoassay), 3rd Ed., Igaku Shoin, 1987, p. 75-126", P. Tijssen, "Enzyme Immunoassay (Seikagaku Jikken-hou (Biochemical Experimentation) 11), Tokyo Kagakudoujin, 1989, p. 196-251", or the like.

As a method of preparing the conjugate based on biological affinity, a method utilizing the binding of avidin and biotin may be used. Examples of this method include a method in which biotin molecules are incorporated into both the same antibody (or its fragment) and another polymer such as albumin, and these are cross-linked via avidin; and a method in which avidin is incorporated into one of the two, and biotin is incorporated into the other, and these are cross-linked with one another. The biotin molecule may be incorporated using biotinyl-ε-aminocaproic acid-N-hydroxysuccinimide ester or the like as a reagent.

As a method for use of the non-specific reaction inhibitor of the present invention, prior to a specific immunological reaction of a target substance with an antibody specific for the target, the non-specific reaction inhibitor may be brought into contact with a sample in an appropriate buffer, and this reaction mixture may be incubated for an appropriate time (for example, for 1 minute to 2 hours) in advance. During the incubation, a substance which causes a non-specific reaction in the sample (a non-specific reaction substance) reacts with the non-specific reaction inhibitor, and the non-specific reaction activity of the non-specific reaction substance to the labeled antibody in the specific immunological reaction is lost.

When an assay method in which the non-specific reaction inhibitor does not affect the specific immunological reaction is used, the mixture of the sample and the non-specific reaction inhibitor after the incubation is completed may be used as is. By contrast, when an assay method in which the non-specific reaction inhibitor affects the specific immunological reaction is used, the non-specific reaction inhibitor after the incubation is completed may be removed from the mixture, before the specific immunological reaction is carried out.

The assay method in which the specific immunological reaction is not affected may be, for example, in a sandwich method which is most commonly used, a method which does not involve an "immobilized antibody-nonspecific reaction substance-labeled antibody" sandwich complex, which is separated in the specific immunological reaction. In this case, more particularly, a non-specific reaction inhibitor (including a free protein, non-separated particles, or the like), which is not separated together with the complex, may be used.

The assay method in which the specific immunological reaction is affected may be, for example, in a sandwich method which is most commonly used, a method which involves an "immobilized antibody-nonspecific reaction substance-labeled antibody" sandwich complex, which is separated in the specific immunological reaction. In this case, more particularly, a non-specific reaction inhibitor (including magnetic particles or the like, when the complex contains similar magnetic particles and is separated by a magnetic force body), which is separated together with the complex, may be used.

As another method for use of the non-specific reaction inhibitor of the present invention, a specific immunological reaction may be carried out in the presence of the non-specific reaction inhibitor. For example, in a sandwich method which is most commonly used, the non-specific reaction inhibitor may be added to a buffer for the first immunological reaction in which an immobilized antibody is reacted with an antigen (a target substance) contained in a sample. The reason why a non-specific reaction is detected is due to the formation of the "immobilized antibody-nonspecific reaction substance-labeled antibody" sandwich complex, not based on the specific reaction site of the antibody. In this case, the reaction activity of the non-specific reaction substance to the labeled antibody is absorbed by the non-specific reaction inhibitor during the first immunological reaction. Further, when the non-specific reaction inhibitor is added to a buffer for the second immunological reaction in which the immobilized antigen captured via the specific reaction site of the antibody is reacted with the labeled antibody, the non-specific reaction substance which has not completely been absorbed in the first immunological reaction is absorbed, and thus, it is possible to further increase the reliability of the measurement.

Similarly as above, although any assay may be used, the assay method in which the specific immunological reaction is not affected is preferable, due to the use of the non-specific reaction inhibitor in the specific immunological reaction.

In a one-step sandwich method, the non-specific reaction can be avoided by adding the non-specific reaction inhibitor to a buffer for an immunological reaction.

Similarly as above, although any assay may be used, the assay method in which the specific immunological reaction is not affected is preferable, due to the use of the non-specific reaction inhibitor in the specific immunological reaction.

Additional timing of the non-specific reaction inhibitor may be appropriately selected in accordance with the target substance or assay method.

For example, the non-specific reaction substance found in the present invention reacts well with the non-specific reaction inhibitor of the present invention, in which a support (in particular, a carrier protein) is coupled directly or indirectly with a maleimide group or its derivative, and thus, the effect is especially high, when a support (in particular, a protein) with which a maleimide group or its derivative is coupled exists during the specific immunological reaction. Therefore, it is most preferable in a reagent prepared by immobilizing or labeling an antibody or antigen using a maleimide method selected among immunoassays.

For example, in the above-mentioned immunoassay using an antibody-containing carrier (an antibody-bound carrier, a labeled antibody, or the like) prepared using a cross-linking agent of the formulae: S-L-M, H-L-M, or X-L-M, the non-specific reaction inhibitor of the formula I may be present in at least one step of the reaction steps. Therefore, the present invention encompasses an immunoassay kit comprising a non-specific reaction inhibitor of the formula I, and an antibody-containing substance prepared using a cross-linking agent of the formulae: S-L-M, H-L-M, or X-L-M. In connection with this, the chemical formulae of the cross-linking agent and the formula I include the same symbol "L", which represents the spacer arm portion, but the structures of the spacer arm portions are different in some cases, in accordance with the type of functional groups S or H or the structure of support B in the cross-linking agent.

The non-specific reaction inhibitor of the present invention may be used by adding it to an appropriate buffer before the immunological reaction or by adding it to a buffer for the immunological reaction. When the support of the non-specific reaction inhibitor is a carrier protein, the concentration of the non-specific reaction inhibitor in the system in which it reacts with the non-specific reaction substance is preferably 0.1 to 1000 μg/mL, and more preferably 1 to 500 μg/mL. The buffer used may be a known and appropriate buffer used in a common immunological reaction. When the support of the non-specific reaction inhibitor is a solid-phase carrier, an artisan skilled in the art can easily select the concentration or the conditions which show the same activity as that of the carrier protein.

Further, the non-specific reaction inhibitor may be used together with additives which are commonly added to the buffers, such as a reaction-promoting agent, a washing agent, or a stabilizer, as well as other non-specific reaction inhibitors. As the appropriate buffer, for example, a 20 to 100 mmol/L phosphate buffer (pH 6-8), a 50 mmol/L Tris-HCl/100 mmol/L NaCl (pH 7-8), or the like may be used. For example, dextran sulfate, polyethylene glycol, or the like may be used as the reaction-promoting agent; TritonX-100, Tween20, or the like may be used as the washing agent; and proteins such as albumin, skim milk, gelatin, or the like, or preservatives such as sodium azide, thimerosal, Kathon CG, ProClin, or the like may be used as the stabilizer.

As for the assay kit comprising the non-specific reaction inhibitor of the present invention, a conventional immunoassay kit may further comprise the non-specific reaction inhibitor. In general, an assay kit based on an ELISA method is composed of reagents such as a labeled antibody solution, an immobilized antibody, a standard, and the like, and further contains, if desired, a buffer for reacting a sample with the immobilized antibody in a sandwich method, a developing solution and a stop solution for an enzyme reaction, a washing solution for washing the solid phase, an agent for sample pretreatment, and the like. When these constituent reagents are freeze-dried products, a solution for restoration may be added in some cases.

The non-specific reaction inhibitor of the present invention may be a constituent reagent by itself, or may be added to another constituent reagent in advance. However, taking into consideration the fact that the effect of inhibiting the non-specific reaction can be obtained without an increase in assay procedures, it is preferable to add it as one component of the constituent reagents. For example, the non-specific reaction inhibitor of the present invention may be a constituent reagent of the kit by adding it to a solution for treating samples, a buffer for the reaction of a sample and immobilized antibody, or a labeled antibody solution. When these constituent reagents are freeze-dried products, it may be added to a solution for restoration. The non-specific reaction inhibitor may be used, preferably by a factor of 0.1 to 1000 by weight, and more preferably by a factor of 1 to 500 by weight, with respect to the labeled antibody.

EXAMPLES

The present invention will now be further illustrated by, but is by no means limited to, the following Examples.

Example 1: Preparation of Non-Specific Reaction Inhibitor (SMCC-BSA)

Bovine serum albumin (BSA: Sigma) was dissolved in 0.1 mol/L HEPES (pH 7.0) so as to become 10 mg/mL. This solution was mixed with a 50 mg/mL Sulfo-SMCC (sulfo-succinimidyl-4-(N-maleimidomethyl)cyclohexane-1-carboxylate)(Pierce) solution in dimethyl sulfoxide (DMSO), and the mixture was allowed to stand at 37° C. overnight. A 114 mg/mL cysteamine HCl solution was added to the resulting reaction solution to block the terminal maleimide group. The resulting product was used as a non-specific reaction inhibitor for the following evaluations.

[Chem. 2]

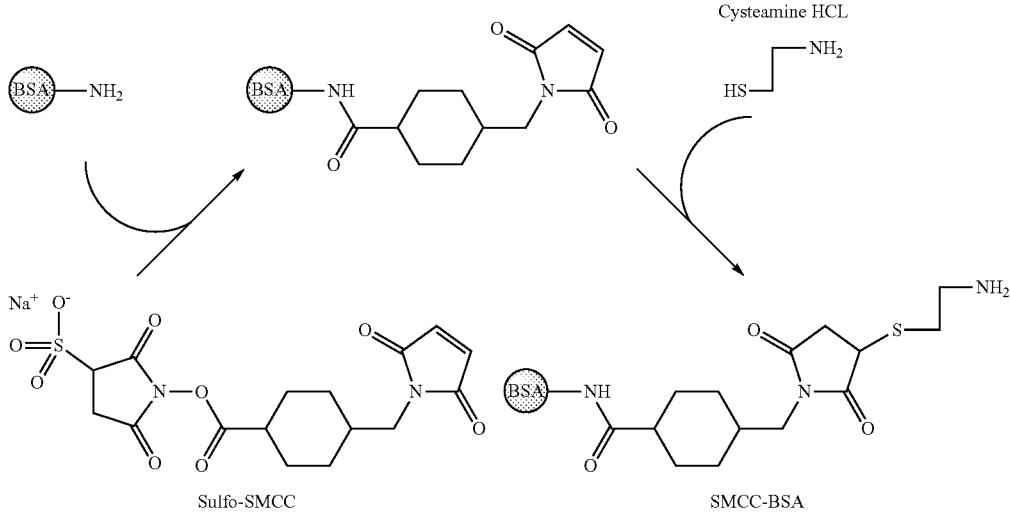

Example 2: Construction of HBs Antigen Measurement System (1) Preparation of Magnetic-Particle-Bound Antibody Solution
(1-1) Magnetic-Particle-Bound Antibody Solution Prepared by Maleimide Method BSA (Sigma) was coupled with magnetic particles (JSR Corporation), and further coupled with an anti-HBs mouse monoclonal antibody, using Sulfo-SMCC (Pierce), to prepare a magnetic particle solution. The anti-HBs mouse monoclonal antibody was prepared by immunizing mice with a recombinant HBs antigen which had been prepared using CH1 cells.

(1-2) Magnetic-Particle-Bound Antibody Solution Prepared by EDC Method

The anti-HBs mouse monoclonal antibody was coupled with magnetic particles (JSR Corporation), using carbodiimide (Sigma), to prepare another magnetic particle solution.

(2) Preparation of Labeled Antibody Solution

An anti-HBs rabbit polyclonal antibody was labeled with alkaline phosphatase (ALP) by a maleimide method to prepare a labeled antibody solution. The anti-HBs rabbit polyclonal antibody was prepared by immunizing rabbits with the recombinant HBs antigen which had been prepared in (1-1).

(3) Luminescent Substrate Solution

Disodium 2-chloro-5-(4-methoxyspiro{1,2-dioxetane-3,2'-(5'-chloro)-tricyclo[$3.3.1.1^{3,7}$]decane}-4-yl)-1-phenyl phosphate (CDP-Star (registered trademark): Applied Biosystems) was used.

(4) Measurement Method

A measurement was carried out using a fully-automated, clinical laboratory system STACIA (Mitsubishi Chemical Medience Corporation).

To 50 µL of each sample, 60 µL of the magnetic-particle-bound antibody solution prepared by a maleimide method or an EDC method was added and heated at 37° C. for 3.5 minutes, and 60 µL of the labeled antibody solution was further added and heated at 37° C. for 8.6 minutes. After a BF separation and washing, 100 µL of the luminescent substrate solution was added and incubated at 37° C. for 2.7 minutes, and the amount of luminescence (counts) was measured after the reaction.

Example 3: Confirmation of the Avoidance Effect of Non-Specific Reaction Inhibitor on Influence of Interfering Substance in Sample In the method described in Example 2, the non-specific reaction inhibitor prepared in Example 1 was added so as to become a final concentration of 0.03%, and the presence or absence of its effects was examined.

One case from HBs-antigen-positive samples, obtained from a patient group that had requested an HBs antigen test, and five cases from HBs-antigen-negative samples, in which a non-specific reaction had been confirmed, were used to carry out measurements under various conditions.

When the magnetic-particle-bound antibody in which the antibody was sensitized by a maleimide method was used, a non-specific reaction was highly observed, in comparison with the case where the magnetic-particle-bound antibody in which the antibody was sensitized by an EDC method (a carbodiimide method) was used. When the non-specific reaction inhibitor was added to the maleimide-method-sensitized magnetic-particle-bound antibody, the non-specific reaction was inhibited significantly.

It was suggested from these results that a non-specific reaction substance, due to the immobilization method on the magnetic particles, was contained in the non-specific samples used for examination. Further, since the non-specific reaction was remarkably observed in a maleimide method, it was predicted that the non-specific reaction occurred against the maleimide group immobilized on the magnetic particles.

TABLE 1

| Sample No. | A | B | C |
| --- | --- | --- | --- |
| Positive sample (Control) | 117178 | — | 128593 |
| Non-specific sample 1 | 9567 | 371 | 433 |
| Non-specific sample 2 | 1068 | 447 | 512 |
| Non-specific sample 3 | 1294 | 251 | 326 |
| Non-specific sample 4 | 810 | 395 | 328 |
| Non-specific sample 5 | 822 | 319 | 383 |

A: Conventional measurement (Sensitized by maleimide method)
B: Conventional measurement (Sensitized by maleimide method) with addition of SMCC-BSA
C: Conventional measurement (Sensitized by EDC method)

Example 4: Examination of Additive Concentration of Non-Specific Reaction Inhibitor The HBs antigen contained in a sample was measured in accordance with Example 2. The SMCC-BSA prepared in Example 1 was added to the magnetic-particle-bound antibody solution in the constituent reagents so as to become concentrations of 0.00003%, 0.0003%, 0.003%, 0.03%, and 0.3%, and the non-specific sample 6, which showed the non-specific reaction as in Example 3, was measured to compare the reactivity. As a result, it was confirmed that the influence due to the non-specific sample could be avoided by adding SMCC-BSA to the magnetic-particle-bound antibody solution at a concentration of 0.0003% or more.

TABLE 2

| SMCC-BSA | 0 | 0.00003% | 0.0003% | 0.003% | 0.03% | 0.3% |
| --- | --- | --- | --- | --- | --- | --- |
| counts | 834 | 614 | 349 | 364 | 319 | 326 |

Example 5: Examination of the Cause of Non-Specific Reaction (1)

The HBs antigen contained in the samples was measured in accordance with Example 2. In order to carry out the following examination, MGLTX (magnetic latex)-BSA-SMCC-Ab, MGLTX-BSA-SMCC, and MGLTX-BSA were prepared as follows.

(1) MGLTX-BSA-SMCC-Ab

BSA (Sigma) was coupled with magnetic particles (JSR Corporation), and further coupled, using Sulfo-SMCC (Pierce), with the anti-HBs mouse monoclonal antibody prepared in Example 2, to prepare a magnetic particle solution.

(2) MGLTX-BSA-SMCC

BSA (Sigma) was coupled with magnetic particles (JSR Corporation), and further coupled with Sulfo-SMCC (Pierce) to prepare a magnetic particle solution.

(3) MGLTX-BSA

BSA (Sigma) was coupled with magnetic particles (JSR Corporation) to prepare a magnetic particle solution.

The magnetic-particle-bound antibody solution in the constituent reagents was replaced with MGLTX-BSA-SMCC-Ab, MGLTX-BSA-SMCC, or MGLTX-BSA, which were made during the preparation process of the antibody-bound magnetic particles, and an HBs-antigen-negative sample and non-specific sample 1 were measured under the following conditions.
(A): (1) alone
(B): (1) with SMCC-BSA (0.03% as final concentration)
(C): (2) alone
(D): (3) alone As a result, an increase in the measured values was observed in the non-specific sample under conditions (A) and (C). In conditions (B), the increase in the measured value under conditions (A) was inhibited by the addition of the non-specific reaction inhibitor (SMCC-BSA) to conditions (A), and the measured value similar to that of the negative sample was obtained. As described above, it was suggested that the cross-linking agent (SMCC) bound to the magnetic particles is deeply involved in the occurrence of the non-specific reaction.

TABLE 3

| Experimental conditions | MGLTX | Negative sample | Non-specific sample 1 |
|---|---|---|---|
| (A) | MGLTX-BSA-SMCC-Ab | 340 | 1184 |
| (B) | MGLTX-BSA-SMCC-Ab (SMCC-BSA added) | 335 | 371 |
| (C) | MGLTX-BSA-SMCC | 335 | 1245 |
| (D) | MGLTX-BSA | 425 | 495 |

Example 6: Examination of the Cause of Non-Specific Reaction (2)

The HBs antigen contained in the samples was measured in accordance with Example 2. In order to carry out the following examination, MGLTX-BSA-SMCC, prepared in a fashion similar to Example 5(2), was further treated with three kinds of blocking agents for a maleimide group to prepare the following magnetic particles, as described below.
(1) Cysteamine (2MEA)

BSA (Sigma) was coupled with magnetic particles (JSR Corporation), followed by Sulfo-SMCC to prepare a magnetic particle solution, and a blocking treatment was carried out with cysteamine (Wako).
(2) Thioglucose BSA (Sigma) was coupled with magnetic particles (JSR Corporation), followed by Sulfo-SMCC to prepare a magnetic particle solution, and a blocking treatment was carried out with thioglucose (Wako).
(3) Mercaptosuccinic Acid BSA (Sigma) was coupled with magnetic particles (JSR Corporation), followed by Sulfo-SMCC to prepare a magnetic particle solution, and a blocking treatment was carried out with mercaptosuccinic acid (Wako).

In the magnetic-particle-bound antibody solution in the constituent reagents, the blocking agent type for a maleimide group, which was used in the preparation of the antibody-bound magnetic particles, was changed to the above-mentioned compounds, and an HBs-antigen-negative sample and non-specific sample 1 were measured. The experimental conditions were as follows:
(A): (1) alone
(B): (1) with SMCC-BSA (0.03% as final concentration)
(C): (2) alone
(D): (3) alone As a result, an increase in the measured values was observed in the non-specific sample under conditions (A), (C), and (D). In conditions (B), the increase in the measured value under conditions (A) was inhibited by the addition of the non-specific reaction inhibitor (SMCC-BSA) to conditions (A), and the measured value similar to that of the negative sample was obtained. Therefore, it was found that the non-specific reaction occurs regardless of the blocking agent type for a maleimide group. As described above, it was suggested that the cross-linking agent (SMCC) bound to the magnetic particles is deeply involved in the occurrence of the non-specific reaction.

TABLE 4

| Experimental conditions | Blocking agent for maleimide group | Negative sample | Non-specific sample 1 |
|---|---|---|---|
| (A) | Cysteamine (2MEA) | 251 | 1299 |
| (B) | Cysteamine (2MEA) (SMCC-BSA added) | 335 | 371 |
| (C) | Thioglucose | 540 | 1322 |
| (D) | Mercaptosuccinic acid | 436 | 1342 |

Example 7: Examination of the Cause of Non-Specific Reaction (3)

The HBs antigen contained in a sample was measured in accordance with Example 2. In order to carry out the following examination, two kinds of non-specific reaction inhibitors, i.e., SMCC-BSA which is blocked with cysteamine HCl as in Example 1, and SMCC-BSA which is not blocked with cysteamine HCl, were prepared. These non-specific reaction inhibitors were added, and a non-specific sample was measured. As a result, it was found that both exhibit the inhibitory effect for the non-specific reaction to the same extent.

As described above, it was found that the non-specific reaction can be inhibited by a carrier protein with a maleimide group.

TABLE 5

| Non-specific reaction inhibitor | Non-specific sample 5 |
|---|---|
| Not added (control) | 822 |
| With blocking | 345 |
| Without blocking | 319 |

INDUSTRIAL APPLICABILITY

The present inventors have shown that the non-specific reaction due to a non-specific reaction substance, which was found in the present invention, occurs at a frequency of 1 per 300 to 1000 samples from healthy persons, regardless of the type of diseases.

According to the non-specific reaction inhibitor, the method of using the same, and the assay kit of the present invention, the influence due to the non-specific reaction substance contained in the samples, which occurs at such a high frequency, can be simply and effectively inhibited, and thus, a trace component contained in the samples can be accurately measured. The present invention is useful for the diagnosis of various diseases.

Although the present invention has been described with reference to specific embodiments, various changes and modifications obvious to those skilled in the art are possible without departing from the scope of the appended claims.

The invention claimed is:

1. An immunological measurement method, said method comprising:
   providing (1) a sample containing a target substance and a non-specific reaction substance capable of binding directly to a maleimide group, (2) a non-specific reaction inhibitor of the formula I:

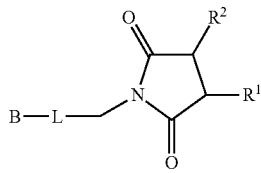

wherein $R^1$ and $R^2$ together form a double bond between carbons to which they are respectively bonded directly, B is a support that is inactive in an assay system, and L is a spacer arm portion having a length of 4 to 20 Å, and (3) a reagent prepared by immobilizing an antibody or an antigen specific for the target substance on a support, or labeling an antibody or an antigen specific for the target substance, by a maleimide method using a cross-linking agent containing a maleimide group;
      treating the sample (1) with the non-specific reaction inhibitor (2), to absorb a non-specific reaction activity of the non-specific reaction substance by the non-specific reaction inhibitor (2), said non-specific reaction substance being contained in the sample (1);
      reacting the treated sample with the reagent (3) to form an immunological complex; and
      analyzing the immunological complex in the immunological measurement method by accounting for the non-specific reaction substance.

2. The immunological measurement method according to claim 1, wherein the immunological measurement method is a latex agglutination optical measurement method, an enzyme immunoassay, a nephelometric immunoassay, an enzyme-linked immunosorbent assay, a fluorescence immunoassay, or a radioimmunoassay.

3. An immunological measurement method, said method comprising:
   providing (1) a sample containing a target substance and a non-specific reaction substance capable of binding directly to a maleimide group, (2) a non-specific reaction inhibitor of the formula I:

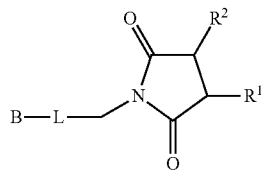

wherein $R^1$ and $R^2$ together form a double bond between carbons to which they are respectively bonded directly, B is a support that is inactive in an assay system, and L is a spacer arm portion having a length of 4 to 20 Å, and (3) a reagent prepared by immobilizing an antibody or an antigen specific for the target substance on a support, or labeling an antibody or an antigen specific for the target substance, by a maleimide method using a cross-linking agent containing a maleimide group;
      reacting the sample (1) with the reagent (3) in the presence of the non-specific reaction inhibitor (2) to form an immunological complex, while absorbing a non-specific reaction activity of the non-specific reaction substance by the non-specific reaction inhibitor (2), said non-specific reaction substance being contained in the sample (1); and
      analyzing the immunological complex in the immunological measurement method by accounting for the non-specific reaction substance.

4. The immunological measurement method according to claim 1, wherein the immunological measurement method is a measurement by a sandwich method, and one or more steps of immunological reactions specific for the target substance contained in the sample is carried out in the presence of the non-specific reaction inhibitor (2).

5. The immunological measurement method according to claim 3, wherein the immunological measurement method is a latex agglutination optical measurement method, an enzyme immunoassay, a nephelometric immunoassay, an enzyme-linked immunosorbent assay, a fluorescence immunoassay, or a radioimmunoassay.

* * * * *